(12) United States Patent
Ochi et al.

(10) Patent No.: US 7,358,726 B2
(45) Date of Patent: Apr. 15, 2008

(54) SYSTEM OF GENERATING A MAGNETIC FIELD AND MRI SYSTEM USING THE SYSTEM OF GENERATING A MAGNETIC FIELD

(75) Inventors: Hisaaki Ochi, Kodaira (JP); Yo Taniguchi, Kokubunji (JP); Hiroyuki Itagaki, Fuchu (JP); Shinichiro Umemura, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 757 days.

(21) Appl. No.: 10/242,442

(22) Filed: Sep. 13, 2002

(65) Prior Publication Data

US 2003/0069497 A1    Apr. 10, 2003

(30) Foreign Application Priority Data

Oct. 10, 2001   (JP) ............................. 2001-312117

(51) Int. Cl.
*G01V 3/00* (2006.01)
(52) U.S. Cl. ...................................................... 324/307
(58) Field of Classification Search ......... 324/300–322
See application file for complete search history.

(56) References Cited

U.S. PATENT DOCUMENTS

| | | | | |
|---|---|---|---|---|
| 4,701,736 A | * | 10/1987 | McDougall et al. | 335/299 |
| 4,714,881 A | | 12/1987 | Givens | |
| 4,721,914 A | | 1/1988 | Fukushima et al. | |
| 4,829,252 A | * | 5/1989 | Kaufman | 324/309 |
| 5,166,619 A | * | 11/1992 | Ries | 324/318 |
| 5,200,701 A | * | 4/1993 | Siebold et al. | 324/309 |

(Continued)

FOREIGN PATENT DOCUMENTS

JP        08-322814        5/1995

(Continued)

OTHER PUBLICATIONS

Richard Ehman; Glossary of MR Terms Fourth Edition, 1995, Commission on Neuroradiology and Magnetic Resonance, pp. 20.*

(Continued)

*Primary Examiner*—Brij Shrivastav
*Assistant Examiner*—Dixomara Vargas
(74) *Attorney, Agent, or Firm*—Reed Smith LLP; Stanley P. Fisher, Esq.; Juan Carlos A. Marquez, Esq.

(57) ABSTRACT

An MRI system using an open type magnet, wherein two coils different in radius for generating gradient magnetic fields in a vertical direction are arranged in the open type magnet for generating a static magnetic field in the vertical direction. Currents are caused to flow through the two coils in directions opposite to each other to improve the degree of uniformity of the magnetic field in the vertical direction, thereby reducing the degradation thereof by equal to or smaller than 2 figures compared with the degree of uniformity of the static magnetic field generated by the existing MRI system. The positional information about a read-out direction is given through the dynamic control for the RF magnetic field to give the positional information about other two axes directions based on the gradient magnetic field having strength much larger than that of nonuniformity of the magnetic field.

13 Claims, 9 Drawing Sheets

U.S. PATENT DOCUMENTS

| | | | |
|---|---|---|---|
| 5,245,286 A * | 9/1993 | Carlson et al. | 324/319 |
| 5,488,342 A * | 1/1996 | Hanley | 335/306 |
| 5,581,187 A * | 12/1996 | Pausch | 324/318 |
| 5,596,303 A * | 1/1997 | Akgun et al. | 335/216 |
| 5,630,415 A * | 5/1997 | Kaufman | 600/422 |
| 5,677,630 A * | 10/1997 | Laskaris et al. | 324/320 |
| 5,744,960 A * | 4/1998 | Pulyer | 324/320 |
| 5,808,467 A | 9/1998 | Ochi et al. | |
| 5,874,831 A * | 2/1999 | Yi et al. | 324/318 |
| 5,914,600 A * | 6/1999 | Pulyer | 324/319 |
| 5,959,454 A * | 9/1999 | Westphal et al. | 324/320 |
| 6,091,241 A * | 7/2000 | Querleux et al. | 324/300 |
| 6,128,522 A * | 10/2000 | Acker et al. | 600/411 |
| 6,144,204 A * | 11/2000 | Sementchenko | 324/318 |
| 6,208,142 B1 * | 3/2001 | Wagshul | 324/319 |
| 6,208,884 B1 * | 3/2001 | Kumar et al. | 600/409 |
| 6,256,526 B1 * | 7/2001 | Butts et al. | 600/410 |
| 6,278,351 B1 * | 8/2001 | Wheatley | 335/299 |
| 6,335,670 B1 * | 1/2002 | Kinanen | 335/296 |
| 6,346,814 B1 * | 2/2002 | Carrozzi et al. | 324/318 |
| 6,522,908 B1 * | 2/2003 | Miyashita et al. | 600/409 |
| 6,539,611 B2 * | 4/2003 | Goto | 29/606 |
| 6,678,544 B2 * | 1/2004 | Butts et al. | 600/410 |
| 6,700,376 B2 * | 3/2004 | Goto et al. | 324/318 |
| 6,801,038 B2 * | 10/2004 | Carrozzi et al. | 324/318 |
| 6,933,722 B2 * | 8/2005 | Tsuda et al. | 324/318 |
| 7,026,816 B2 * | 4/2006 | Gebhardt et al. | 324/318 |
| 7,034,537 B2 * | 4/2006 | Tsuda et al. | 324/320 |
| 7,144,376 B2 * | 12/2006 | Nakai et al. | 600/508 |
| 2004/0162480 A1 * | 8/2004 | Satragno et al. | 600/415 |
| 2005/0258924 A1 * | 11/2005 | Xia | 335/296 |

FOREIGN PATENT DOCUMENTS

| | | | |
|---|---|---|---|
| JP | 09-019410 | | 7/1995 |
| JP | PUB 09-019410 | * | 1/1997 |
| JP | 10-057344 | | 7/1997 |
| JP | 10-057345 | | 7/1997 |
| JP | 10-057346 | | 7/1997 |
| WO | WO 90/05986 | | 11/1989 |

OTHER PUBLICATIONS

Kensuke Sekihara, Shigeru Matsui and Hideki Kohno, "NMR Imaging for Magnets with Large Nonuniformities", IEEE (1985), pp. 193-199.

JPO Office Action mailed Jul. 31, 2007, in Japanese.

* cited by examiner

SYSTEM OF GENERATING A MAGNETIC FIELD AND MRI SYSTEM USING THE SYSTEM OF GENERATING A MAGNETIC FIELD

BACKGROUND OF THE INVENTION

1. Field of the Invention

The present invention relates in general to an open type magnetic field generating system arranged only below a bed which should be loaded with an object to be inspected, and an MRI (Magnetic Resonance Imaging) system using the same. More particularly, the invention relates to a magnetic field generating system suitable for an interventional MRI system and a system using the same.

2. Description of the Related Art

The terms which will be used in the following description are defined as follows:

"Composite magnetic field": A magnetic field which is obtained by composing a static magnetic field generated by means for generating a static magnetic field and a gradient magnetic field in a vertical direction.

"Nonuniformity of a static magnetic field": A difference between maximum magnetic field strength and minimum magnetic field strength of a static magnetic field in an imaging area.

"The degree of uniformity of a static magnetic field": A value which is obtained by dividing "nonuniformity of a static magnetic field" by a mean magnetic field strength of a static magnetic field in an imaging area.

"Nonuniformity of a composite magnetic field": A difference between maximum magnetic field strength and minimum magnetic field strength of a composite magnetic field in an imaging area.

"The degree of uniformity of a composite magnetic field": A value which is obtained by dividing "nonuniformity of a composite magnetic field" by mean magnetic field strength of a composite magnetic field in an imaging area.

A method which is most effective for reduction in medical cost is to shorten an in-hospital period of time. It is expected to dramatically shorten a period of time for medical treatment in a hospital due to the spread of a low invasive operation such as an operation under use of an endoscope or a low ultrasound coagulation therapy. In particular, an MRI system (e.g., JP-A-10-57344, JP-A-10-57345, and JP-A-10-57346: the prior art-1) which has a wide opening part to be able to access a patient from a multi-direction by a user (doctor) is regarded as the most powerful system for realization of the low invasive operation because there is no problem in the radiation exposure and hence it is expected to make an interventional MRI system fit for practical use. FIG. 2 is a perspective view showing an example of a conventional MRI system having a wide opening part. In the figure, there are shown static magnetic field generating means 210 arranged in a upper position and static magnetic field generating means 200 arranged in a lower position which face each other in a vertical direction.

The level of uniformity of a static magnetic field required for a conventional MRI system is equal to or lower than 10 ppm in an area of about 30 cm. On the other hand, for the purpose of acquiring MR images under the nonuniform static magnetic field, there are known a method of reducing distortion in an image utilizing a magnetic field map which is previously measured (K. Sekihara: "NMR Imaging for Magnets with Large Nonuniformities", IEEE, TRANSACTIONS ON MEDICAL IMAGING, Vol. MI-4, No. 4, December 1985, pp. 193 to 199: the prior art-2), and a method of giving positional information by controlling dynamically an RF magnetic field (JP-A-8-322814: the prior art-3, JP-A-9-019410: the prior art-4).

Though the open degree of the conventional MRI system shown in FIG. 2 is higher than that of any of general MRI systems in which a static magnetic field is formed in a tunnel type space, it is difficult to carry a large operation tool or a system of ultrasound coagulation therapy between the static magnetic field generating means arranged in a upper position and the static magnetic field generating means arranged in a lower position, and hence it is required from a user (doctor) to further increase the open degree. If the construction is adopted in which the static magnetic field generating means 210 arranged in the upper position and shown in FIG. 2 is removed and the magnet (the static magnetic field generating means 200) arranged only in the lower position (hereinafter, referred to as "the open type magnet" for short, when applicable) is used to realize an MRI system having the higher open degree (hereinafter, referred to as "an open type MRI system" for short, when applicable), then large operation tools or a system of ultrasound coagulation therapy can be used readily.

The most important problem when the open type magnet is used is to realize the degree (equal to or smaller than 10 ppm in an area of about 30 cm in a vertical direction) of uniformity of a static magnetic field having the level required for the conventional MRI system. In the open type magnet using only the lower magnet placed on a floor, the degree of uniformity of a static magnetic field becomes about 10% even in an area of 20 cm in a vertical direction, which leads to the degradation the degree of which is about 10,000 times (four figures) as large as that of the existing MRI system.

In general, while if there is the nonuniformity in distribution of a static magnetic field, this leads to the distortion or blurring of an MR image, or a lack of a signal, when the uniformity of a static magnetic field is degraded so as to become about 10,000 times as large as that of the existing MRI system, it is difficult to acquire a nuclear magnetic resonance signal itself. If the methods of the prior arts-2, -3 and -4 are utilized, then even when the degree of uniformity of a static magnetic field is degraded by equal to or larger than one figure as compared with the existing MRI system, it is possible to acquire an image having less distortion. However, when the degree of uniformity of a static magnetic field is degraded by four figures as compared with the existing MRI system, it is difficult to apply any of the methods of the prior arts-2, -3 and -4.

The correction technique for reducing the image distortion utilizing the magnetic field map shown in the prior art-2 is the correction technique which is established on the assumption that the strength of a read-out gradient magnetic field is much larger that that of nonuniformity of a static magnetic field. For this reason, if the strength of the gradient magnetic field is made equal to that of the existing one, the limit of the correction application is as far as the degradation of the degree of uniformity of a static magnetic field which is worse by about one figure at the most as compared with the existing one. While if the strength of the field of the gradient magnetic field is strengthened, then the correction application can be applied to the magnet as well having the larger nonuniformity of a static magnetic field, if the strength of the read-out gradient magnetic field is increased, then the wider measurement band is required when receiving a signal. The S/N ratio of the measured signal is degraded in proportion to the square root of the measurement band.

The degree of uniformity of a static magnetic field in the open type magnet in a vertical direction is degraded by about four figures as compared with that of uniformity of a static magnetic field generated by the existing MRI system. As a result, in the open type MRI system using the open type magnet, it is difficult to acquire the positional information in a vertical direction. The open type MRI system using the open type magnet has the problem of improving the nonuniformity of the static magnetic field in the vertical direction.

With the method of giving the positional information by controlling dynamically the RF magnetic field shown in the prior art-3 or the prior art-4, since no gradient magnetic field is used, with respect to one-axis direction, even if the degree of uniformity of a static magnetic field is degraded by equal to or larger than two figures as compared with the existing one, it is possible to acquire the positional information. However, with respect to the remaining two-axes directions, it is necessary to give the positional information on the basis of the gradient magnetic field, and hence the distortion occurs in the positional information in the remaining two-axes directions. The open type MRI system using the open type magnet has the problem of giving accurately the positional information.

SUMMARY OF THE INVENTION

In the light of the foregoing, the present invention has been made in order to solve the above-mentioned problems associated with the prior art, and it is, therefore, an object of the present invention to provide an open type magnetic field generating system in which even if the degree of uniformity of a static magnetic field is degraded, the S/N ratio is not largely degraded and hence an image having less distortion can be imaged, and which is arranged only below a bed which should be loaded with an object to be inspected, and an open type MRI system using the same.

A magnetic field generating system according to the present invention for use in an MRI system is arranged only below a bed which should be loaded with an object to be inspected. The magnetic field generating system includes: as static magnetic field generating means, magnets facing each other in a horizontal direction and magnetically coupled to each other, or coils having respective faces facing each other in a horizontal direction, the magnets or the coils serving to generate a static magnetic field in a horizontal direction; or a magnet for generating a static magnetic field in a vertical direction or a static magnetic field generating coil. In addition, the magnetic field generating system includes a gradient magnetic field generating coil for generating a gradient magnetic field in a vertical direction. The gradient magnetic field generating coil is constituted by a first coil and a second coil with which the first coil is enclosed, and the first and second coils are arranged either on a plane or a curved surface. The gradient magnetic field generating coil is arranged either on or above the means for generating a static magnetic field.

Currents are respectively caused to flow through the first and second coils in directions opposite to each other, and hence the direction of a magnetic field generated by the first coil is opposite to that of a magnetic field generated by the second coil. The currents are respectively caused to flow through the first and second coils in the directions opposite to each other, whereby the degree of uniformity of the static magnetic field generated by the means for generating a static magnetic field is improved to suppress the degradation of the degree of uniformity of a composite magnetic field of the static magnetic field and the gradient magnetic field in a vertical direction by equal to or smaller than two figures as compared with the degree of uniformity of the static magnetic field of the existing MRI system.

The first and second coils are arranged either on the same plane or on the same curved surface (a recess-like curved surface or a convex-like curved surface), or the first and second coils are respectively arranged either on the different planes or on the different curved surfaces. Each of the first and second coils has either a circular shape, or a deformed 8-like shape, and also has a circular shape having a discontinuous part in one direction to be arranged in a concentric configuration. The radii of the first and second coils are equal to or larger than 15 cm, but equal to or smaller than 35 cm.

In the MRI system using the magnetic field generating system according to the present invention, the positional information with respect to the directions is given as follows. A receiving RF coil is dynamically controlled to change the distribution of sensitivity of the receiving RF coil along a time basis a plurality of times to give the positional information with respect to a read-out direction. The gradient magnetic field having the much larger strength than that of nonuniformity of the static magnetic field (corresponding to the gradient larger than that of nonuniformity of the static magnetic field by at least equal to or larger than two figures) is applied to give the positional information with respect to the remaining two directions (i.e., a slice direction and a phase encoding direction). More specifically, the MRI system of the present invention includes: means for generating a static magnetic field in a vertical direction; a bed which should be loaded with an object to be inspected in the space where the static magnetic field is generated; a first gradient magnetic field coil having a first coil and a second coil with which the first coil is unclosed, the first and second coils being arranged on a plane or on a curved surface, the coil serving to generate a gradient magnetic field in a vertical direction; a second gradient magnetic coil for generating a gradient magnetic field, in a slice direction, having larger strength than that of the nonuniformity of the static magnetic field; a third gradient magnetic field coil for generating a gradient magnetic field, in a phase encoding direction, having larger strength than that of nonuniformity of the static magnetic field; and a receiving RF coil for changing the distribution of sensitivity along a time basis a plurality of times to give positional information with respect to a read-out direction. In the MRI system of the present invention, the first gradient magnetic field coil and the means for generating the static magnetic field are both arranged below the bed, the currents are respectively caused to flow through the first and second coils in the directions opposite to each other, and hence the direction of the magnetic field generated by the first coil is opposite to that of the magnetic field generated by the second coil. In addition, the radii of the first and second coils are equal to or larger than 15 cm, but equal to or smaller than 35 cm.

Other objects, features and advantages of the invention will become apparent from the following description of the embodiments of the invention taken in conjunction with the accompanying drawings.

DESCRIPTION OF THE EMBODIMENTS

The preferred embodiments of the present invention will hereinafter be described in detail with reference to the accompanying drawings.

Figure 1:
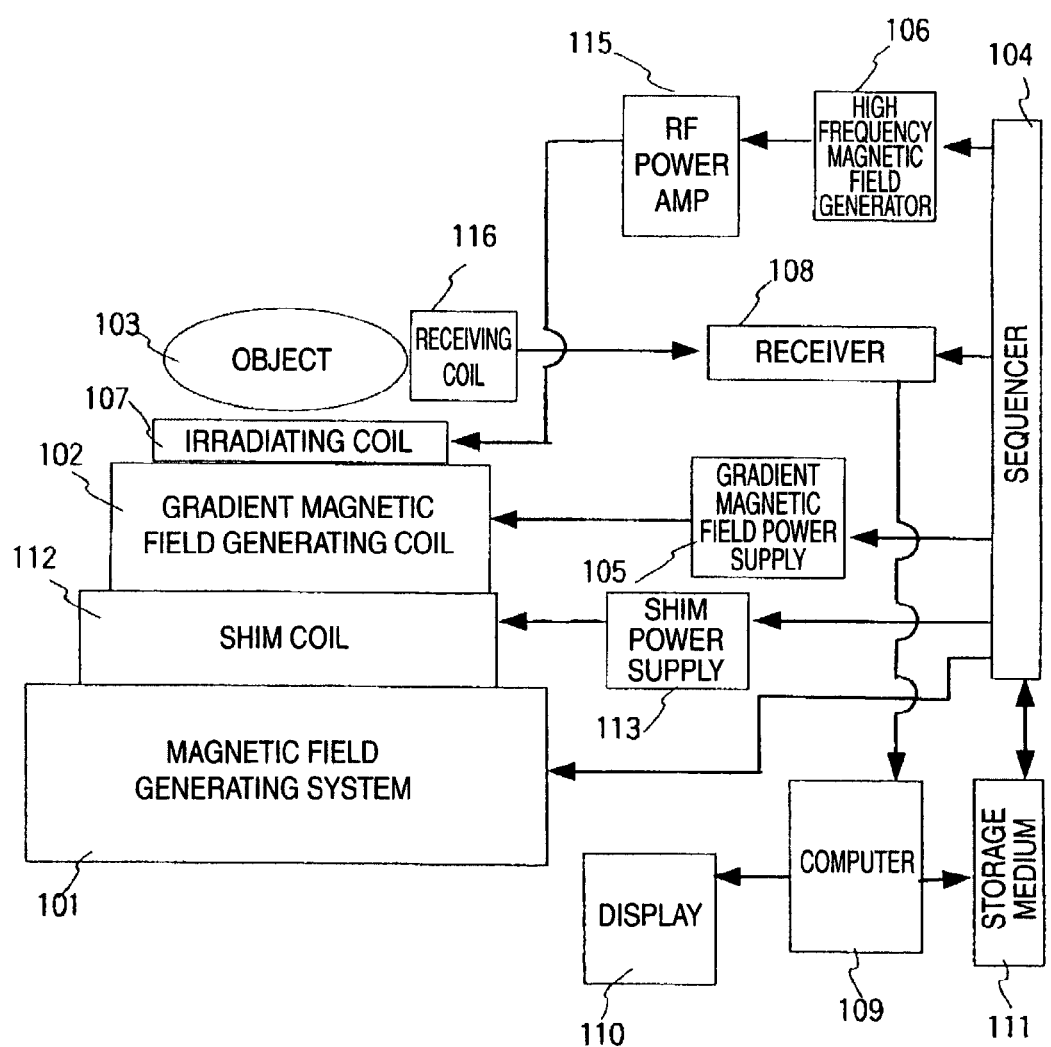
FIG. 1 is a block diagram showing a configuration of an example of an MRI system according to the present invention.

An MRI system is a system for measuring a tomographic image of an object to be inspected utilizing the nuclear magnetic resonance. FIG. 1 is a block diagram showing an example of a configuration of the MRI system according to the present invention. Referring now to FIG. 1, an object to be inspected (object) 103 is placed above a magnetic field generating system 101 including means for generating a static magnetic field, and a coil for generating a gradient magnetic field in a vertical direction, and a gradient magnetic field coil 102 for generating gradient magnetic fields in two directions perpendicular to a vertical direction. A bed 220, 230 which should be loaded with the object 103 to be inspected is arranged over the gradient magnetic field coil 102. The means for generating a static magnetic field is comprised of magnets coupled magnetically to each other so as to face each other in a horizontal direction or a pair of coils having faces facing each other which they make with each other in the horizontal direction for generating a static magnetic field in the horizontal direction, or a magnet or a static magnetic generating coil placed on a floor for generating a static magnetic field in the vertical direction.

A sequencer 104 issues instructions to the gradient magnetic field power source 105 and an RF pulse generator 106, respectively, to instruct the gradient magnetic field coil 102 and an irradiating coil 107 to generate the gradient magnetic fields in two directions perpendicular to the vertical direction, and an RF pulse, respectively. In addition, the sequence 104 also issues an instruction to a gradient magnetic field power source (not shown) to instruct coils 41-1 and 41-2, or 41'-1 and 41'-2 to generate a gradient magnetic field in the vertical direction. Furthermore, the sequencer 104 may also issue an instruction to a magnetic field power source (not shown) to instruct a pair of static magnetic field generating coils 91-1 and 91-2 to generate the static magnetic field in some cases.

Normally, an output signal from the RF pulse generator 106 is amplified in an RF power amplifier 115 to apply the resultant RF pulse to the object 103 to be inspected through the irradiating coil 107. A nuclear magnetic resonance signal which has been generated from the object 103 to be inspected is received by a receiving coil 116. The irradiating coil 107 is arranged either in the space defined between the bed 220, 230 which should be loaded with the object 103 to be inspected and the magnet 300, 301 (or a pair of static magnetic field generating coils 91-1 and 91-2) or in the inside of the bed 220, 230. The receiving coil 116 is arranged in the space close to a part to be inspected (a part to be imaged) of the object 103 to be inspected.

The receiving coil 116 may be inserted into the inside of the object 103 to be inspected in same cases. The signal which has been received by the receiving coil 116 is the subjected to the A/D conversion (sampling) processing and the detection processing in the receiver 108. The central frequency (the magnetic resonance frequency) as the reference for the detection is set by the sequencer 104. After the detected signal is sent to a computer 109 to be subjected to the sampling processing therein, the signal processing such as the image reconfiguration is executed. The result of the image reconfiguration or the like is delayed on a display 110.

If necessary, a signal or measurement conditions may also be stored in a storage medium 111. When there is the necessity of adjusting the degree of uniformity of a static magnetic field, a shim coil 112 is used. The shim coil 112 includes a plurality of channels and currents are supplied from a shim power source 113 thereto. In adjusting the degree of uniformity of the static magnetic field, the currents which are respectively caused to flow through coils of a plurality of channels are controlled by the sequencer 104. The sequencer 104 issues an instruction to the shim power source 113 to instruct the shim coil 112 to generate an additional magnetic field used to correct the nonuniformity of the static magnetic field.

By the way, the sequencer 104 carries out the control in such a way that the apparatuses operate at the programmed timing and at the programmed strength. Of these programs, in particular, one in which the application of the RF pulse, the application of the gradient magnetic field, the timing at which the nuclear magnetic resonance signal should be received, and the RF pulse and the strength of the gradient magnetic field are described is called the imaging sequence.

First Embodiment

In a first embodiment, the description will hereinbelow be given with respect to a magnetic field generating system using an open type magnet for generating a static magnetic field in a vertical direction, and an open type MRI system using the same.

Figure 2:
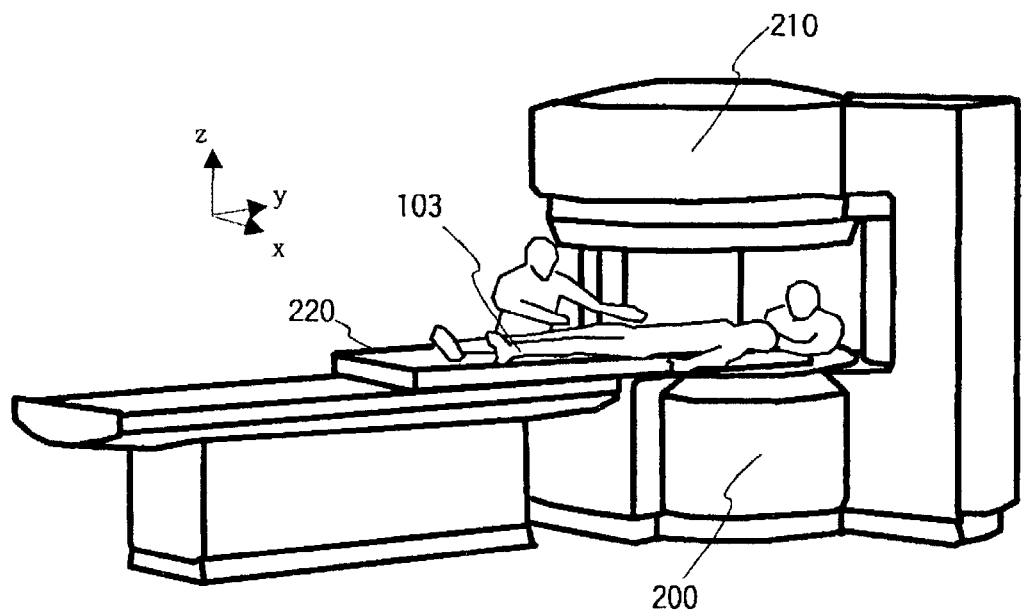
FIG. 2 is a perspective view showing an example of a conventional MRI system having a wide opening part.
Figure 3:
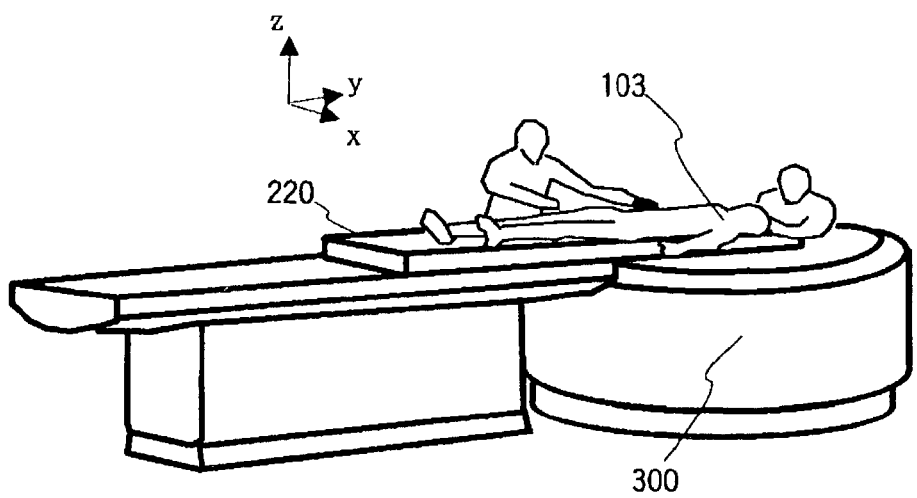
FIG. 3 is a perspective view showing an example of an open type MRI system according to the present invention.

FIG. 3 is a perspective view showing an example of an open type MRI system according to the present invention. In the open type MRI system shown in FIG. 3, an open type magnet 300 which has the external appearance in which the static magnetic field generating means 210 shown in FIG. 2 and arranged in the upper position is removed, which is placed on a floor, and which serves to generate a static magnetic field in a vertical direction is used as the magnetic field generating system 101.

As shown in FIG. 3, the bed 220 which has a flat shape in the x-y plane and on which the object to be inspected should be placed is arranged above an open type magnet 300 in the vertical direction, and a part to be inspected of the object 103 to be inspected is arranged in the space 5 to 25 cm away from the open type magnet 300 in the vertical direction. A top board of the bed 200 which should be loaded with the object 103 to be inspected is movable on a stage for supporting the top board in the x and y directions.

Figure 11:
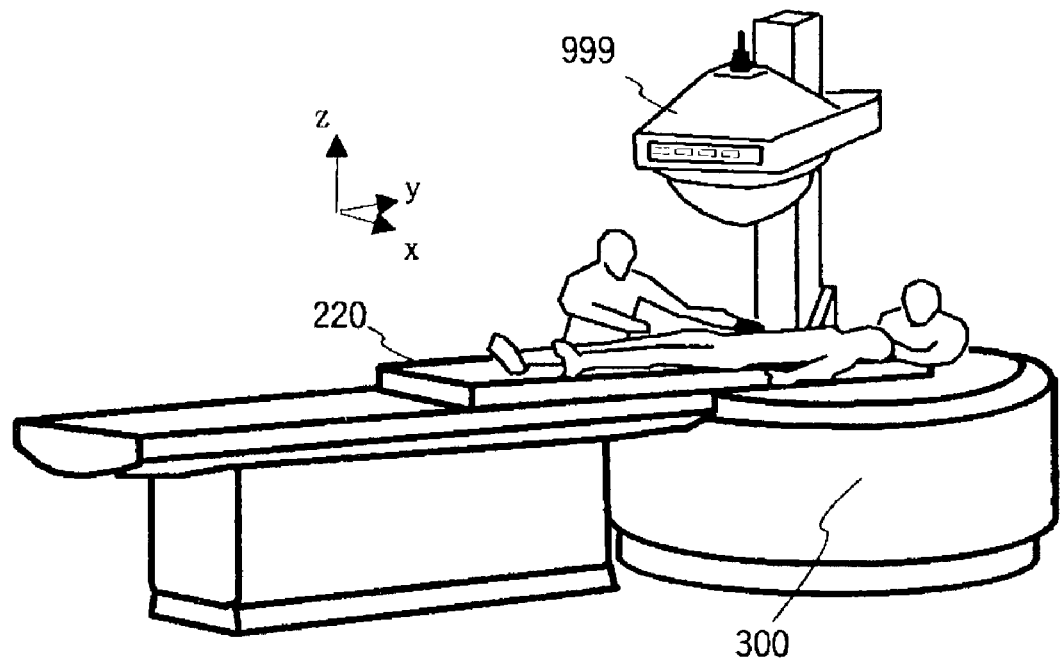
FIG. 11 is a perspective view showing an example of construction in which a system of ultrasound coagulation therapy is arranged in the open type MRI system of the present invention.
Figure 12:
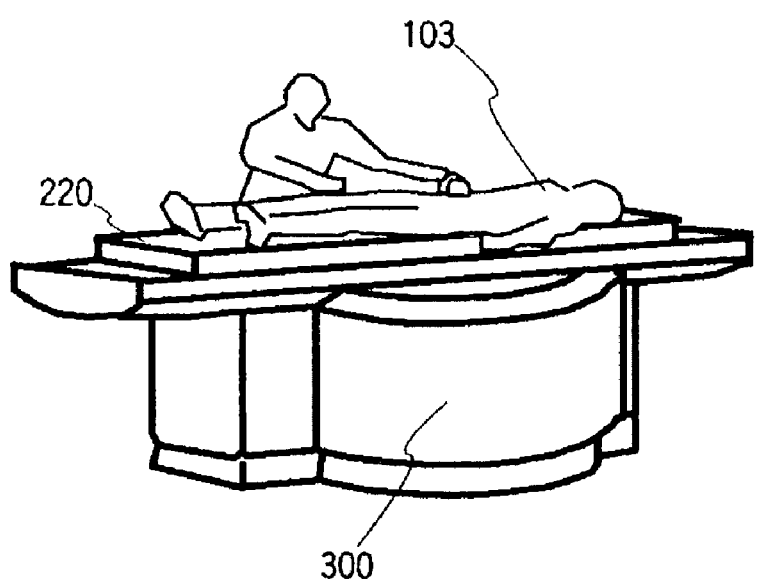
FIG. 12 is a perspective view showing another example of the open type MRI system of the present invention.

Since the magnet is present only below the object 103 to be inspected, as shown in FIG. 11, it becomes possible to arrange a large system 999 of ultrasound coagulation therapy above the object 103 to be inspected. Likewise, it is also possible to arrange a laser medical treatment apparatus, a robot manipulator for operation or the like above the object 103 to be inspected. In addition, if the open type magnet 300 and the bed 220 are arranged so as to have □ the positional relationship as shown in FIG. 12, then it is possible to further compact the size of the whole system. In the construction shown in FIGS. 11 and 12, the object 103 to be inspected is lying down on the bed 220, and a part to be inspected of the object to be inspected is arranged in the space above the open type magnet 300. The bed 220 is made of a non-magnetic material. The top board of the bed 220 which should be loaded with the object 103 to be inspected is movable on the stage for supporting the top board in the x and y directions.

Now, the vertical direction is decided as the z-axis direction, and the direction of the body axis of the object 103 to be inspected is decided as the y-axis direction. The shape of the open type magnet 300 on the x-y plane is made a round shape, and the radius of the circle is set to 50 cm. The center of the circle is decided as x=y=0, the upper end of the open type magnet 300 is decided as z=0, and the upper part with respect to the open type magnet 300 is decided as the positive direction of the z-axis.

In this open type magnet 300, in the range of 5 cm<z<25 cm in the area of the radius of 10 cm in the vicinity of the center of the x-y plane, the strength of the static magnetic field decreases linearly along the z-axis direction (the strength of the static magnetic field in the position of z=5 cm is assumed to be 1T). At this time, the strength of the static magnetic field in the position of z=25 cm becomes 0.7T. If the degree of uniformity of the static magnetic field in the z-axis direction is about +18%, and the degree of uniformity of the static magnetic field of the existing MRI system is +10 ppm, then the degree of uniformity of the static magnetic field is degraded by equal to or larger than four figures.

Figure 4A:
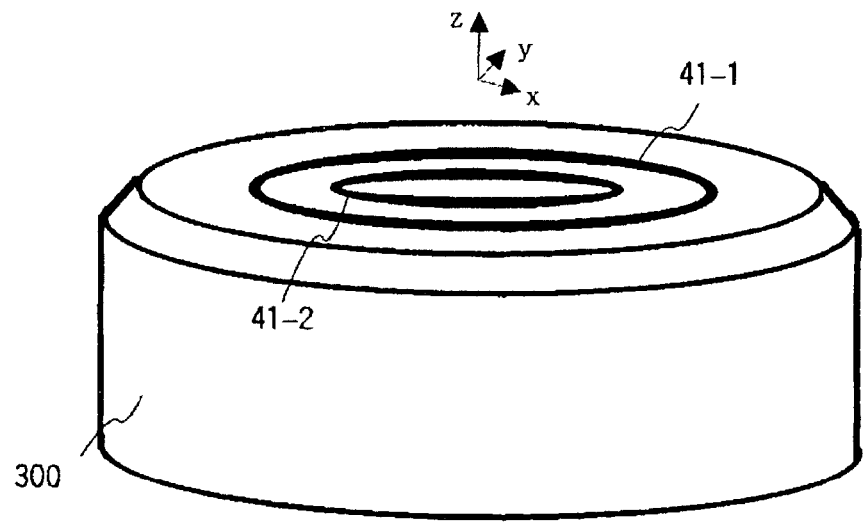
FIGS. 4A an 4B are respectively views showing construction of a magnetic field generating system of a first embodiment according to the present invention and showing an example of arrangement of a circular magnet and a gradient magnetic field coil.
Figure 4B:
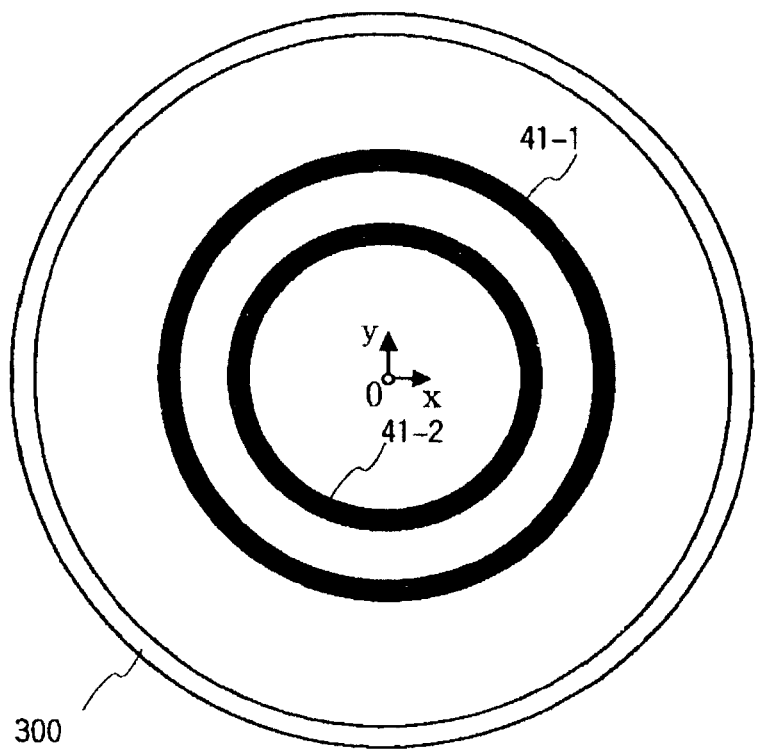

FIGS. 4A and 4B are respectively views each showing construction of the magnetic field generating system of the first embodiment according to the present invention and also views showing an example of arrangement of a circular magnet and a gradient magnetic field coil in the vertical direction (in the z-axis direction). FIG. 4A is a perspective view and FIG. 4B is a plan view.

In order to improve the degree of uniformity of the static magnetic field in the z-axis direction, as shown in FIGS. 4A and 4B, the gradient magnetic field coil in the z-axis direction is constituted by two coils 41-1 and 41-2 different in radius from each other and currents are caused to flow through the two coils in directions opposite to each other.

Then, it is assumed that the two coils are constructed in a concentric configuration, and the radius of the coil 41-1 is 30 cm and the radius of the coil 41-2 is 20 cm. The two coils 41-1 and 41-2 are arranged in such a way that the center thereof matches the central axis of a cylinder of a cylindrical open type magnet 300. The bed 220 is arranged above the gradient magnetic field coils 41-1 and 41-2 in the z-axis direction.

Figure 5:
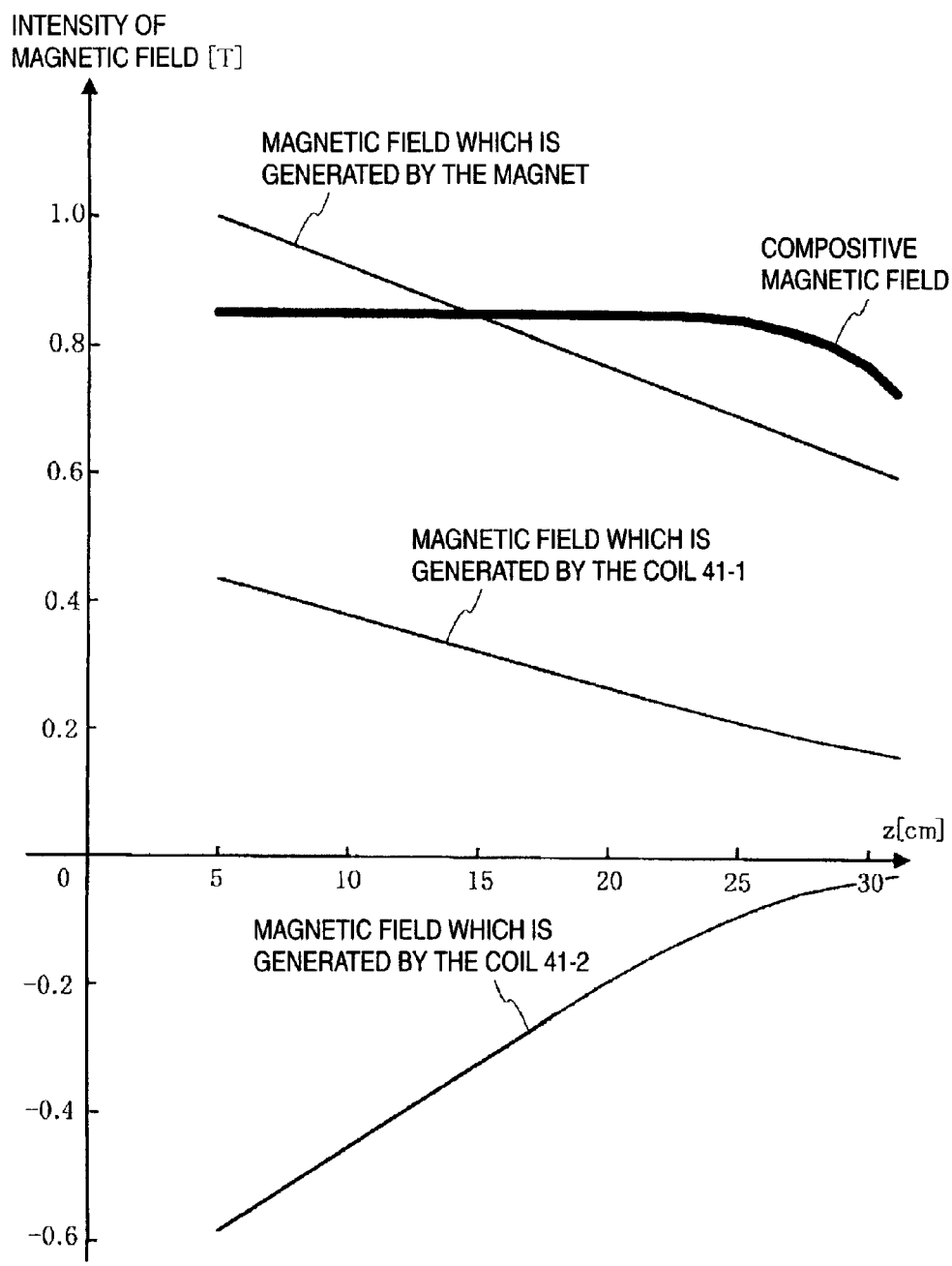
FIG. 5 is a graphical representation useful in explaining an example of calculation for a magnetic field generated by a magnetic field generating system having an open type magnet and a coil in the first embodiment according to the present invention.

FIG. 5 is a graphical representation useful in explaining an example of calculation for the magnetic fields generated by the magnetic field generating system having the open type magnet 300 and the coils 41-1 and 41-2. In the range of 5 cm<z<25 cm in the area of the radius of 10 cm in the vicinity of the center of the x-y plane, either the strength of the magnetic fields which are respectively generated by the two coils 41-1 and 41-2 changes roughly in a linear fashion along the z-axis direction. Then, the polarity of the magnetic field generated by the coil 41-1 is positive, while the polarity of the magnetic field generated by the coil 41-2 is negative, and either strength of the magnetic fields generated by the coils 41-1 and 41-2 decreases. At this time, the currents which are respectively caused to flow through the coils are set in such a way that the strength of the magnetic field which is generated in the position of z=5 cm by the coil 41-1 becomes 0.43T, and the strength of the magnetic field which is generated in the position of z=5 cm by the coil 41-2 becomes −0.58T. If the number of turns of the coil 41-1 is 540, and the number of turns of the coil 41-2 is 505, then either of the values of the currents which are caused to flow through the coil 41-1 and the coil 41-2, respectively, becomes about 400A.

Let us consider the composite magnetic field which is obtained by composing the magnetic field generated by the open type magnet 300 and the magnetic fields generated by the coils 41-1 and 41-2. In the range of 5 cm<z<25 cm in the area of the radius of 10 cm in the vicinity of the center of the x-y plane, the degree of uniformity of the composite magnetic field is enhanced and hence the degree of uniformity of the composite magnetic field becomes equal to or smaller than ±1,000 ppm with 0.85T as the center. This value is degraded by two figures as compared with the degree of uniformity of the existing MRI system. As shown in FIG. 5, either of the magnetic fields generated by the coils changes firstly linearly along the z-axis direction and approach zero by and by. The z-coordinate of the point of inflection is small as the size of the coils are smaller. The polarity of the magnetic field generated by the coil 41-2 is positive, while the polarity of the magnetic field generated by the coil 41-2 is negative, and either strength of the magnetic fields generated by the coils 41-1 and 41-2, respectively, decreases.

Since when the object to be inspected is lying down on the bed 220, the thickness of the object 103 to be inspected is about 20 cm, the desired value of the radii of the coils 41-1 and 41-2 is in the range of 15 to 35 cm because the degree of uniformity of the composite magnetic field is wanted to be enhanced in the range of at least z<20 cm. The state in which the composite magnetic field is most uniform is decided as the steady state and the magnitudes of the currents caused to flow through the coils 41-1 and 41-2 are increased or decreased, whereby it is possible to generate the gradient magnetic field in the vertical direction. For example, in the case where either of the magnitudes of the currents caused to flow through the coils 41-1 and 41-2 is made zero, the composite magnetic field becomes equivalent to the magnetic field generated by the open type magnet 300. The strength of the gradient magnetic field in the vertical direction at this time becomes about 1500 mT/m. This value is larger than the strength of the gradient magnetic field used in the existing MRI system by about two figures. By the way, the shape of each of the coils 41-1 and 412 shown in FIG. 4 may also be polygonal instead of being circular.

Figure 6:
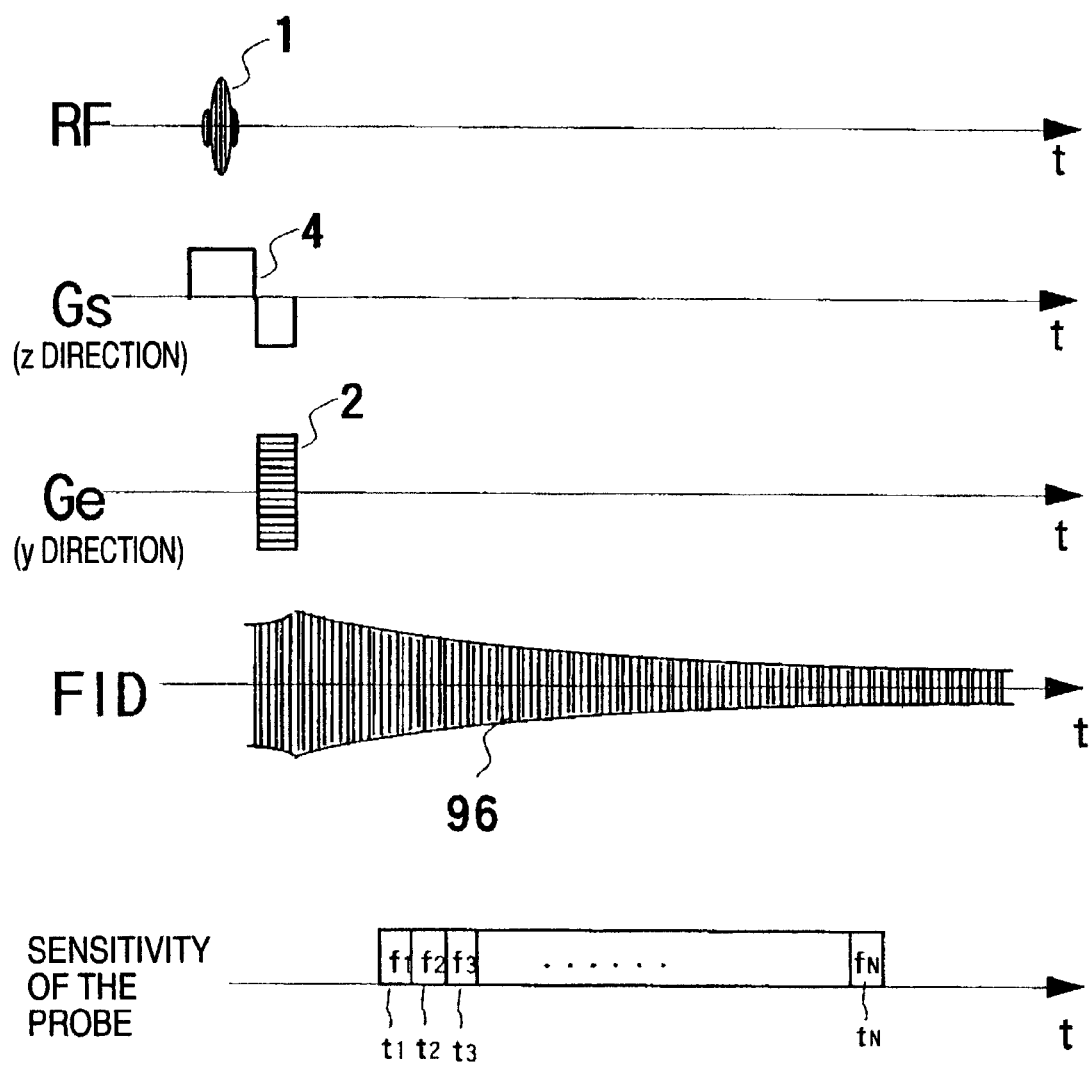
FIG. 6 is a view useful in explaining an example of an imaging sequence in the first embodiment according to the present invention.

FIG. 6 is a view showing an example of the imaging sequence in the first embodiment according to the present invention. In this case, the z-direction is selected as the slice direction, the x-direction is selected as the read-out direction and the y-direction is selected as the phase encoding direction. A slice gradient magnetic field Gs (the gradient magnetic field in the z-axis direction) 4 and a phase encoding gradient magnetic field Ge (the gradient magnetic field in the y-axis direction) 2 are both used as the gradient magnetic fields. First of all, the slice gradient magnetic field 4 and an exciting RF magnetic field 1 are applied at the same time to excite the atomic nuclei which are present in the inside of the slice cross section having a desired thickness.

As described above, the degree of uniformity of the composite magnetic field generated by the magnetic field generating system for use in the open type MRI system is degraded by two figures as compared with the existing MRI system. For this reason, if the imaging is carried out using the strength of the slice gradient magnetic field used in the existing MRI system, then the slice cross section does not become a plane, but becomes a curved surface. This curved surface becomes a configuration corresponding to the distribution of the nonuniform composite magnetic field. This impedes remarkably that a doctor grasps the positional information in the inside of an object to be inspected. The strength of the slice gradient magnetic field is increased by two figures as compared with the strength thereof used in the existing MRI system, whereby it is possible to set the slice having distortion of the same degree as that in the slice cross section used in the existing MRI system.

Now, the description will hereinbelow be given with respect to a method of acquiring a two-dimensional image. The positional information (projection) of the object to be inspected in the read-out direction (x-direction) is obtained by the dynamic control (the dynamic control for changing the distribution of sensitivity of the receiving RF coil along a time basis) for the RF magnetic field disclosed in the prior art-3 or the prior art-4. That is to say, an FID (Free Induction Decay) signal 96 is measured a plurality of times to reconfigure a one-dimensional image while changing the distribution of sensitivity of the receiving RF coil (probe) a plurality of times along a time basis. FIG. 6 shows that the distribution of sensitivity of the probe is changed so as to become preset functions f1, f2, . . . , fN at time t1, t2, . . . , tN of the signal measurement. The distribution of sensitivity of receiving RF coil is given an inclination and also the sensitivity distribution thereof is changed, whereby it is possible to carry out the control for giving the positional information in the inclination direction (read-out direction) of this sensitivity distribution. The sensitivity distribution is changed in such a way that a matrix expression of a sensitivity matrix which is defined by the functions f1, f2, . . . , fN expressing the sensitivity distribution of the probe changing with time does not become zero (refer to the prior art-3), or the sensitivity distribution of the receiving RF coil (probe) is changed a plurality of times with time in accordance with Wavelet basis function (refer to the prior art-4), whereby it is possible to reconfigure the projection in a specific direction of the object to be inspected.

With the imaging method of giving the positional information in the read-out direction by the gradient magnetic field, if the strength of the readout gradient magnetic field is increased, then the wide measurement band is required when receiving a signal. The S/N ratio of the measured signal is degraded in proportional to the measurement band to half power. In the present invention, since the positional information of read-out is acquired through the dynamic control for the RF magnetic field (the dynamic control for the sensitivity distribution of the receiving RF coil), the read-out gradient magnetic field is unnecessary to allow the measurement band to be narrow. As a result, the degradation of the S/N ratio resulting from the strengthening of the strength of the gradient magnetic field is less.

When the number of pixels of the two-dimensional image to be reconfigured in the phase encoding direction is 128, the procedure for obtaining the above-mentioned projection is repeated while changing an application quantity of phase encoding gradient magnetic field Ge (2) 128 times in a step-like manner and changing the sensitivity distribution of the receiving RF coil (probe) along a time basis. The resultant 128 projections are Fourier-transformed in the direction of application of the phase encoding gradient magnetic field to obtain the two-dimensional image. In the present invention, with respect to one-axis direction of three-axes directions, the phase information is acquired through the dynamic control for the RF magnetic field (the dynamic control for the sensitivity distribution of the receiving RF coil). With respect to other two-axes directions, even if the degree of uniformity of the composite magnetic field generated by the magnetic field generating system using the open type magnet is degraded by two figures as compared with the degree of uniformity of the static magnetic field generated by existing MRI system, if the strength of the gradient magnetic field is strengthened by two figures,then the distortion in an image is almost equal to that in the existing MRI system. Though when the strength of the gradient magnetic field can be strengthened by only about one figure from the reason that the capacity of the gradient magnetic field power source is wanted to be suppressed small and so forth, distortion occurs in an image, this distortion can be removed or reduced in accordance with the prior art-2. In the prior art-2, the distribution of the nonuniform static magnetic field is previously measured. The MR image which has been acquired under the nonuniform static magnetic field contains therein the distortion in an image and the change in concentration value due to the nonuniformity of the magnetic field. Then, the influences of the nonuniformity of the magnetic field (the distortion in an image and the change in concentration value due to the nonuniformity of the magnetic field) are corrected utilizing the distribution of the static magnetic field (magnetic field map) to remove these influences from the image containing therein these influences of nonuniformity of the magnetic field.

If the flip angle of an irradiating RF magnetic field 1 is set equal to or smaller than 10 degree and TR (repeated time) is set to 2 msec., then at a two-dimensional image is obtained after a lapse of 256 msec. The moving picture can be displayed in real time if the imaging is carried out while replacing the data newly measured with respect to a certain quantity of applied Ge with the data with respect to a quantity of same applied Ge before one round.

While in an example shown in FIG. 6, the positional information (projection) of the object to be inspected in the read-out direction is obtained through the dynamic control for the RF magnetic field (the dynamic control for the sensitivity distribution of the receiving RF coil), if the area concerned (field of view) is limited to equal to or smaller than 10 cm, then the image having less distortion can be acquired utilizing the magnetic field map shown in the prior art-2 and using the correction technique for reducing image distortion. This reason is that if the area concerned (field of view) is decreased, then the degradation of the degree of uniformity of the composite magnetic field generated by the magnetic field generating system using the open type magnet can be reduced by equal to or smaller than one figure as compared with that of the degree of uniformity of the static magnetic field generated by the existing MRI system. In this case, though there is the defect that the field of view is reduced, there is offered the effect that the special receiving RF coil with which the dynamic control for the sensitivity distribution can be carried out becomes unnecessary.

Figure 7:
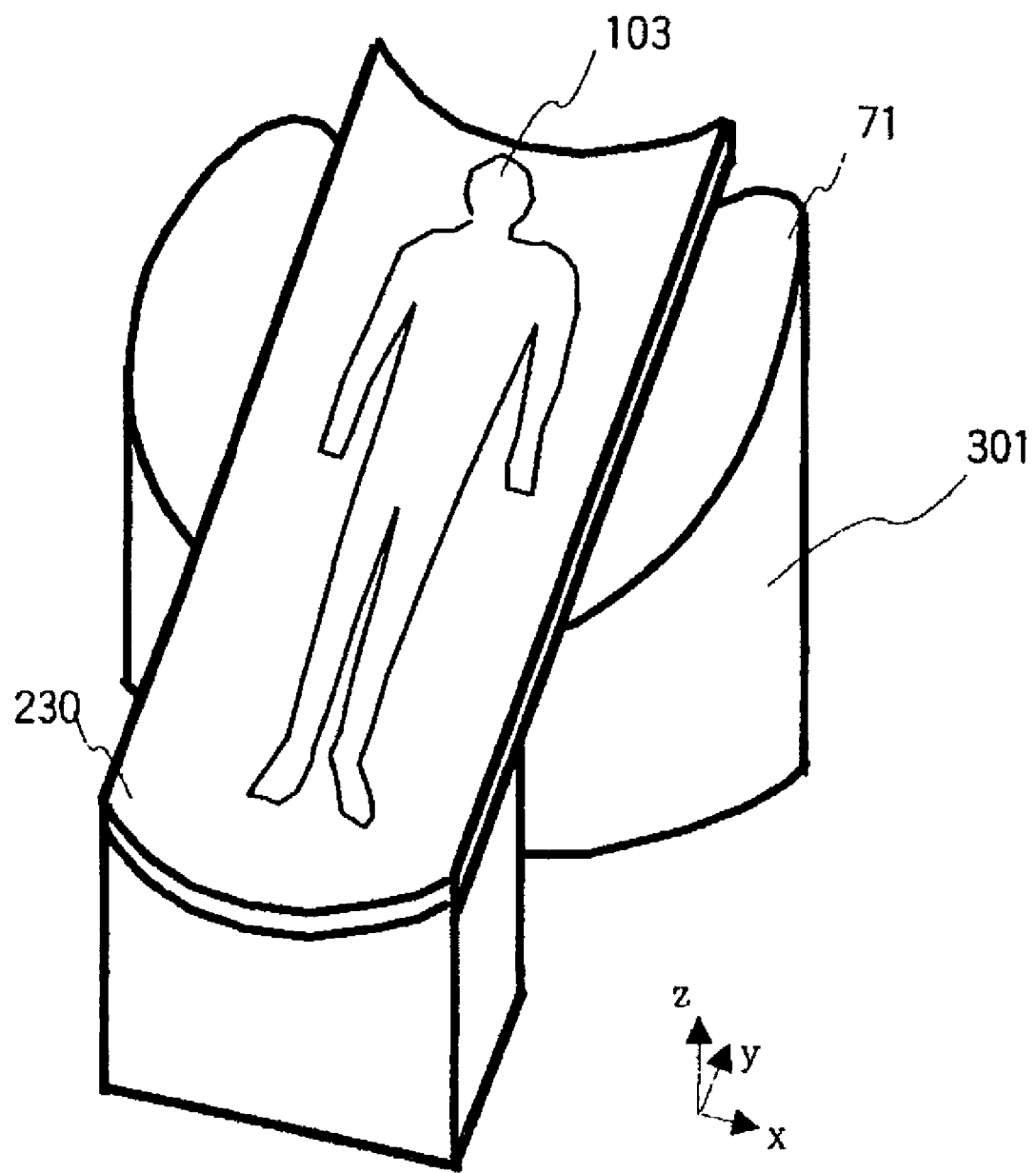
FIG. 7 is a view showing an example of shape of an open type magnet for use in the magnetic field generating system in the first embodiment of the present invention.

In addition, while in the example shown in FIG. 4, the description was given with respect to the example in which the object to be inspected is lying down in the space above the open type magnet 300 having flat shape on its upper surface (x-y plane), as shown in FIG. 7, the upper surface of the open type magnet 301 for generating the static magnetic field in the vertical direction for use in the magnetic field generating system 101 is shaped into a recess-like curved surface 71, whereby it is possible to increase the area of the uniform space of the composite magnetic field or the area of the linear space of the gradient magnetic field. In this case, the magnet element and the gradient magnetic field coil constituting the magnetic field generating system 101 as has previously been described are both shaped into a curved surface along the recess-like curved surface 71. The object 103 to be inspected is lying down on the bed 230 having the recess-like curved surface fitted to the recess-like curved surface 71 and a part to be inspected of the object to be inspected is arranged in the space above the open type magnet 301. The bed 220, 230 is made of a non-magnetic material. The top board of the bed which should be loaded with the object 103 to be inspected is movable on the top board supporting stage in the x and y directions.

Second Embodiment

In a second embodiment, the description will hereinbelow be given with respect to the magnetic field generating system 101 for generating a static magnetic field in a horizontal direction.

Figure 8:
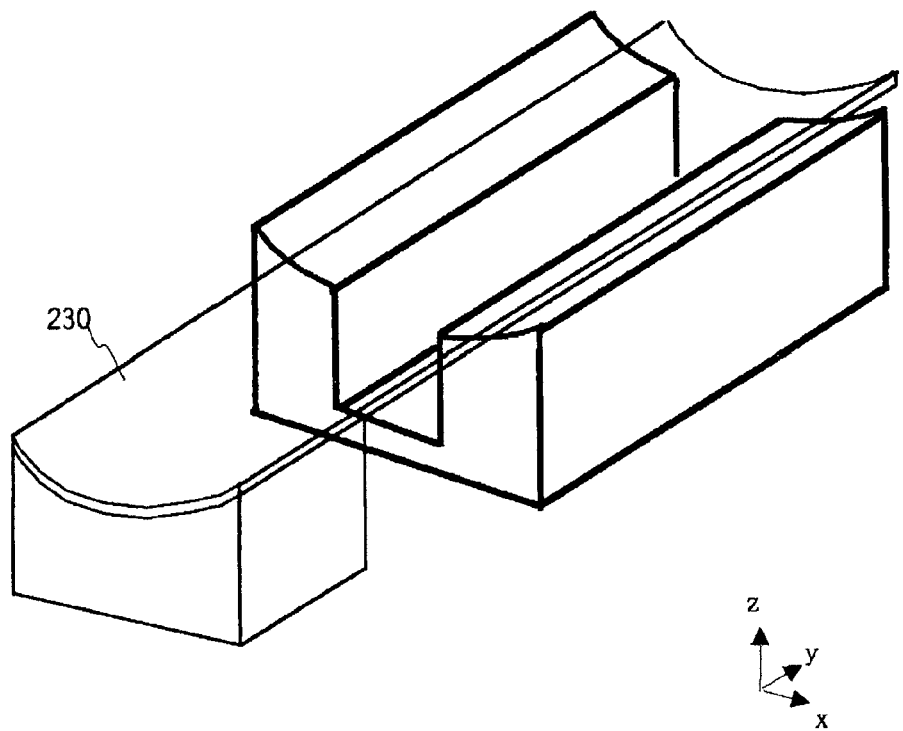
FIG. 8 is a perspective view showing an example of shape of an open type magnet for use in a magnetic field generating system in a second embodiment of the present invention.

FIG. 8 is a perspective view showing an example of shape of the open type magnet for use in the magnetic field generating system 101 in the second embodiment according to the present invention. As for an open type magnet for generating a static magnetic field in a horizontal direction, as shown in FIG. 8, there are used two permanent magnets which face each other in a horizontal direction and which are magnetically coupled to each other. The two permanent magnets are enclosed with a chassis (not shown) and the bed 230 is arranged in the space above the chassis.

Figure 9:
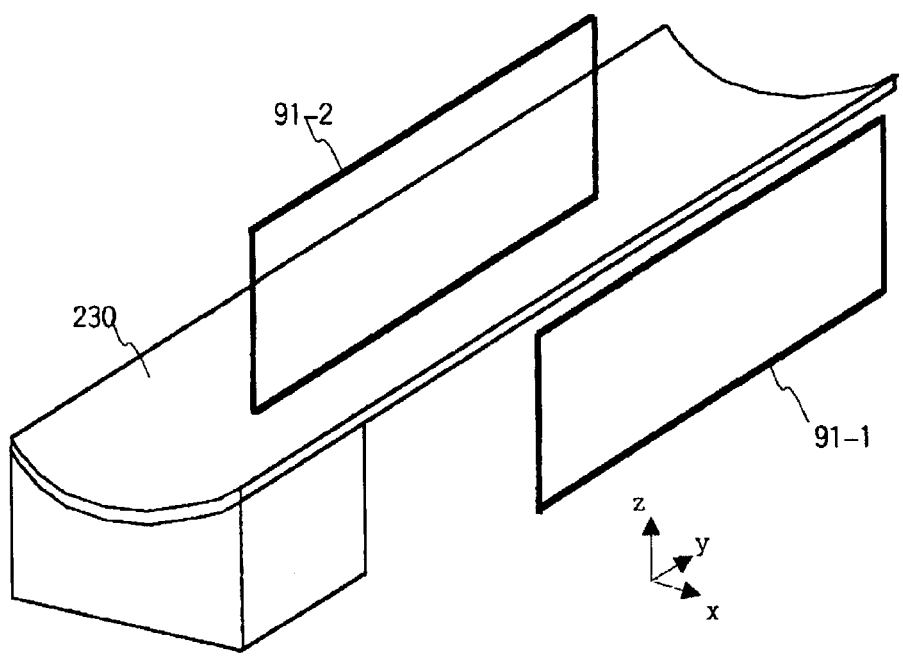
FIG. 9 is a perspective view showing an example of arrangement of a pair of static magnetic field generating coils for use in the magnetic field generating system in the second embodiment of the present invention.

FIG. 9 is a perspective view showing an example of arrangement of a pair of static magnetic field generating coils 91-1 and 91-2 for use in the magnetic field generating system in the second embodiment according to the present invention. The static magnetic field generating coils 91-1 and 91-2 are both enclosed with a chassis (not shown) and are supported by the chassis, and the bed 230 is arranged in the space above this chassis.

Figure 10:
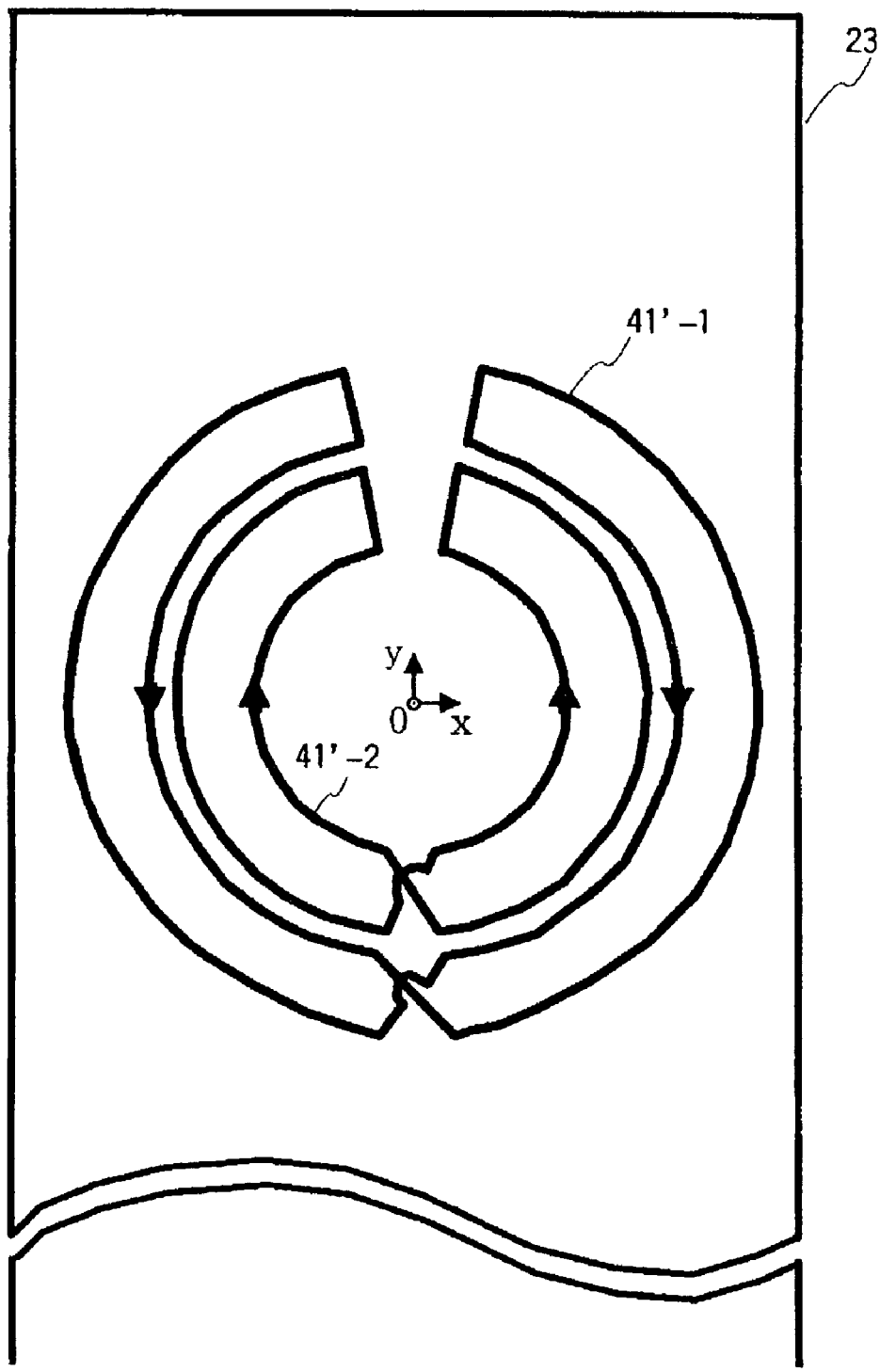
FIG. 10 is a view showing an example of a gradient magnetic field coil which is applied to the second embodiment of the present invention.

In the static magnetic field as well which is generated either by the open type magnet (refer to FIG. 8) used in the magnetic field generating system 101 of the second embodiment or by the static magnetic field generating coils (refer to FIG. 9), the degree of uniformity of the static magnetic field in the vertical direction (z-axis direction) is degraded by equal to or larger than four figures as compared with the degree of uniformity of the static magnetic field in the existing MRI system. In order to improve the degree of uniformity of the static magnetic field in the z-axis direction, as shown in FIG. 10, the gradient magnetic field coil in the z-axis direction is constituted by two coils 41'-1 and 41'-2 different in radius from each other and currents are respectively caused to flow through the two coils 41'-1 and 41'-2 in directions opposite to each other. The two coils 41'-1 and 41'-2 are deformed 8-like coils each having a discontinuous part in the y direction and having circular shape as a whole to be arranged in a concentric configuration. By the way, it is assumed that the diameter of the coil 41'-1 is 30 cm and the diameter of the coil 41'-2 is 20 cm.

In the area of the radius of 10 cm in the vicinity of the center of the x-y plane, the coils 41'-1 and 41'-2 generate the magnetic field in the x direction and the magnetic field in the −x direction, respectively. In the range of 5 cm<z<25 cm, either the strength of the magnetic fields which are respectively generated in the x and y directions by the two coils 41'-1 and 41'-2 changes roughly in a linear fashion along the z-axis direction. The strength of the magnetic field generated by the coil 41'-2 changes more steeply, along the z-axis direction, than that of the magnetic field generated by the coil 41'-1.

Similarly to the description in the first embodiment, the currents which are respectively caused to flow through the two coils 41'-1 and 41'-2 are suitably set, whereby in the range of 5 cm<z<25 cm in the area of the radius of 10 cm in the vicinity of the center of the x-y plane, it is possible to enhance the degree of uniformity of the magnetic field which is obtained by composing the magnetic field generated either by the magnet or the static magnetic field coil, and the magnetic fields generated by the coils 41'-1 and 41'-2, respectively, i.e., the degree of uniformity of the composite magnetic field. In addition, the state in which that composite magnetic field is the most uniform is decided as the steady state, and either magnitude of the currents which are respectively caused to flow through the coils 41'-1 and 41'-2 are increased or decreased, whereby it is possible to generate the gradient magnetic field in the vertical direction. By the way, each of the coils 41'-1 and 41'-2 shown in FIG. 10 may be of 8-like shape, and also the whole shape may also be polygonal instead of being circular.

In the open type MRI system using the magnetic field generating system and shown in FIG. 8 or in FIG. 9, the bed 230 which should be loaded with the object 103 to be inspected is arranged either in the space above the two permanent magnets facing each other in the horizontal direction as shown in FIG. 8, or in the space above a pair of static magnetic field generating coils 91-1 and 91-2 as shown in FIG. 9. A part to be inspected of the object to be inspected is arranged in the space where the composite magnetic field is generated by the magnetic field generating system. The top board of the bed 230 which should be loaded with the object 103 to be inspected is movable on the top board supporting stage at least in the y direction.

The two permanent magnets facing each other in the horizontal direction, or a pair of static magnetic field generating coils 91-1 and 91-2 are arranged in the direction perpendicular to the major-axis direction of the bed 230. Making the comparison with the magnetic field generating system 101 using the open type magnet 300 of the first embodiment shown in FIG. 3, since the magnetic field generating system 101 of the second embodiment as shown in FIG. 8 or 9 has the flat shape on the both side faces, there is offered the effect that a doctor can readily approach an object to be inspected from the side thereof. That is to say, a doctor can approach an object to be inspected from the direction perpendicular to the body axis of an object to be inspected.

While in each of the examples shown in FIGS. 8 to 10, the object 103 to be inspected lies down on the bed 230 having the recess-like curved surface shown in FIG. 7, the construction may also be adopted in which the object 103 to be inspected lies down on the bed 220 having the flat shape shown in FIG. 3.

In addition, similarly to the description in the first embodiment, with respect to the read-out direction, the positional information is acquired utilizing the method of giving the positional information through the dynamic control for the RF magnetic field, and with respect to the remaining two directions, the positional information is given on the basis of the gradient magnetic field having much larger strength than that of nonuniformity of the static magnetic field (the gradient which is larger than that of nonuniformity of the static magnetic field by at least equal to or larger than two figures), whereby it is possible to obtain a two-dimensional image.

Though above, the present invention has particularly shown and described with reference to the preferred embodiments, with respect to the embodiments as well other than the above-mentioned first and second embodiments, likewise, with respect to the read-out direction, the positional information is acquired utilizing the method of giving the positional information through the dynamic control for the RF magnetic field, and with respect to the remaining two directions, the positional information is given on the basis of the gradient magnetic field having much larger strength than that of nonuniformity of the static magnetic field (the gradient which is larger than that of nonuniformity of the static magnetic field by at least equal to or larger than two figures), whereby it is possible to obtain a tomographic image of an object to be inspected by using the open type MRI system.

In addition, it is to be understood that a permanent magnet, an electromagnet, or super-conducting magnet may be used as the magnet for generating the static magnetic field in a horizontal or vertical direction. Furthermore, it is to be understood that as the means for generating the static magnetic field, the static magnetic field generating coil for generating the static magnetic field in the vertical direction which is constructed by winding a resistive coil or super-conducting coil round an axis extending in the vertical direction may be arranged on a floor below the bed to be used.

Since there is no means for generating a static magnetic field above an object to be inspected, there is offered the effect that it is possible to install a large operation tool or system of ultrasound coagulation therapy above an object to be inspected. That is to say, there is offered the effect that a system meeting user's needs can be provided in an interventional MRI system. For example, while in the imaging sequence shown in FIG. 6, the method of acquiring a two-dimensional image has been described, the imaging sequence can be readily extended to the imaging of a three-dimensional image by utilizing the known technique in the field of the MRI system.

As set forth hereinabove, according to the present invention, it is possible to provide an open type MRI system which is capable of imaging an image having less distortion (tomographic image of an object to be inspected) since even if the degree of uniformity of a composite magnetic field obtained from a magnetic field generating system arranged only below an object to be inspected is degraded, the S/N ratio is not largely degraded. Also, it is possible to arrange a large operation tool or an apparatus (or a system) for medical treatment above an object to be inspected since there is no means for generating a static magnetic field above an object to be inspected.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A magnetic field generating system, comprising:
   means for generating a static magnetic field;
   a gradient magnetic field generating coil having a first coil and a second coil with which said first coil is enclosed, for generating a gradient magnetic field in a vertical direction; and
   a bed on which an object to be inspected is laid, wherein said means for generating a static magnetic field and said gradient magnetic field generating coil are both arranged only below said bed, and the direction of the magnetic field generated by said first coil is opposite to that of the magnetic field generated by said second coil, and an upper surface of said means for generating a static magnetic field has a recess-like curved surface, and said gradient magnetic field coil is arranged along said recess-like curved surface.

2. A magnetic field generating system according to claim 1, wherein each of said first and second coils has a circular shape.

3. A magnetic field generating system according to claim 2, wherein said first and second coils are arranged in a concentric configuration.

4. A magnetic field generating system according to claim 2, wherein the radii of said first and second coils are equal to or larger than 15 cm, but equal to or smaller than 35 cm.

5. A magnetic field generating system according to claim 1, wherein said means for generating a static magnetic field has either magnets facing each other in a horizontal direction, or coils having faces facing each other, in a horizontal direction.

6. A magnetic field generating system according to claim 1, wherein said means for generating a static magnetic field has either a magnet for generating a static magnetic field in a vertical direction, or a static magnetic field generating coil.

7. A magnetic field generating system, comprising:
   means for generating a static magnetic field; and
   a gradient magnetic field generating coil having a first coil and a second coil with which said first coil is enclosed, said first and second coils being arranged either on a plane or on a curved surface, said gradient magnetic field generating coil serving to a generate a magnetic field in a vertical direction,
   wherein said means for generating a static magnetic field and said gradient magnetic field generating coil are both arranged only below a bed for being loaded with an object to be inspected in an MRI system, and the direction of the magnetic field generated by said first coil is opposite to that of the magnetic field generated by said second coil, and each of said first and second coils has a deformed 8-like shape and also has circular shape having a discontinuous part in one direction.

8. A magnetic field generating system according to claim 7, wherein said first and second coils are arranged in a concentric configuration.

9. A magnetic field generating system according to claim 7, wherein the radii of said first and second coils are equal to or larger than 15 cm, but equal to or smaller than 35 cm.

10. A magnetic field generating system, comprising:
   means for generating a static magnetic field either in a horizontal direction or in a vertical direction;
   a gradient magnetic field generating coil having two circular coils different in radius from each other for generating a gradient magnetic field in the vertical direction; and
   a bed on which an object to be inspected is laid,
   wherein said means for generating a static magnetic field and said gradient magnetic field generating coil are both arranged only below said bed, and the directions of the magnetic fields which are respectively generated by said two coils are opposite to each other, an upper surface of said means for generating a static magnetic field has a recess-like curved surface, and said gradient magnetic field coil is arranged along said recess-like curved surface.

11. A magnetic field generating system according to claim 10, wherein the radii of said two coils are equal to or larger than 15 cm, but equal to or smaller than 35 cm.

12. An MRI system, comprising:
   means for generating a static magnetic field in a vertical direction;
   a bed for being loaded with an object to be inspected in a space where the static magnetic field is generated;
   a first gradient magnetic field generating coil having a first coil and a second coil with which said first coil is enclosed for generating a gradient magnetic field in a vertical direction;
   a second gradient magnetic field generating coil for generating a gradient magnetic field, in a slice direction, having larger strength than that of nonuniformity of the static magnetic field;
   a third gradient magnetic field generating coil for generating a gradient magnetic field, in a phase encoding direction, having larger strength than that of nonuniformity of the static magnetic field; and
   a receiving RF coil for changing sensitivity distribution a plurality of times along a time basis to give positional information with respect to a read-out direction,
   wherein said first gradient magnetic field generating coil and said means for generating a static magnetic field are both arranged only below said bed, and the direction of the magnetic field generated by said first coil is opposite to that of the magnetic field generated by said second coil, and an upper surface of said means for generating a static magnetic field has a recess-like curved surface, and said gradient magnetic field coil is arranged along said recess-like curved surface.

13. An MRI system according to claim 12, wherein the radii of said first and second coils are equal to or larger than 15 cm, but equal to smaller than 35 cm.

* * * * *